(12) United States Patent
Harding et al.

(10) Patent No.: US 7,656,996 B2
(45) Date of Patent: Feb. 2, 2010

(54) DEVICE AND METHOD FOR MAPPING THE DISTRIBUTION OF AN X-RAY FLUORESCENCE MARKER

(75) Inventors: Geoffrey Harding, Hamburg (DE); Gerhard Martens, Henstedt-Ulzburg (DE); Hans Barschdorf, Dassendorf (DE); Bernd Schweizer, Herzogenrath (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 165 days.

(21) Appl. No.: 10/598,003

(22) PCT Filed: Feb. 11, 2005

(86) PCT No.: PCT/IB2005/050535
§ 371 (c)(1),
(2), (4) Date: May 20, 2008

(87) PCT Pub. No.: WO2005/083406
PCT Pub. Date: Sep. 9, 2005

(65) Prior Publication Data
US 2008/0226025 A1    Sep. 18, 2008

(30) Foreign Application Priority Data
Feb. 20, 2004   (EP)   ................. 04100687

(51) Int. Cl.
*G01T 1/36* (2006.01)

(52) U.S. Cl. .................................. 378/49; 378/44
(58) Field of Classification Search .............. 378/44–50
See application file for complete search history.

(56) References Cited

U.S. PATENT DOCUMENTS

| 4,839,913 | A  | * | 6/1989  | Annis et al. ................. 378/44 |
| 5,497,407 | A  |   | 3/1996  | Komatsu et al. |
| 2008/0267348 | A1 | * | 10/2008 | Puusaari et al. ............ 378/44 |

FOREIGN PATENT DOCUMENTS

EP   0766083 A   4/1997

OTHER PUBLICATIONS

Takeda et al; "Fluorescent Scanning X-Ray Tomography with Synchrotron Radiation," 1995, Rev. Sci. Instrum. vol. 66, pp. 1471-1473.

* cited by examiner

*Primary Examiner*—Hoon Song

(57) ABSTRACT

The invention relates to a method and a device for determining the distribution of an X-ray fluorescence (XRF) marker (16) in a body volume (14). The body volume (14) is irradiated with a beam of rays (12) from an X-ray source (10) with a first ray component with a quantum energy just above and a second ray component with a quantum energy just below the K-edge of the XRF marker (16). Secondary radiation emitted from the body volume (14) is detected in a location-resolved way by a detector (30). To separate the X-ray fluorescence components in the secondary radiation from background radiation, the body volume is irradiated for a second time with a beam of rays from which the first ray component has been substantially removed by a filter (22) made from the material of the XRF marker.

10 Claims, 2 Drawing Sheets

DEVICE AND METHOD FOR MAPPING THE DISTRIBUTION OF AN X-RAY FLUORESCENCE MARKER

The invention relates to a device and a method for mapping the distribution of an X-ray fluorescence marker in a body volume, wherein the fluorescence of the marker is excited by an X-ray source.

A method for molecular imaging has been described in literature, wherein X-ray fluorescence radiation of an atom with a high atomic number integrated into a drug is observed (Takeda et al., "Fluorescent scanning X-ray tomography with synchrotron radiation", 1995, Rev. Sci. Instrum. Vol. 66, pages 1471-1473). X-ray fluorescence (XFR) is generated when an electron from an energetically higher quantum level falls onto a site on a lower quantum level, which has previously been freed by primary X-rays of sufficiently high quantum energy. As the spectrum of the emitted XRF photons is characteristic for the emitting element and the intensity of the spectral lines is proportional to the mass of the XRF marker, the spatial distribution of even low concentrations of the marker can be detected with a high degree of sensitivity using a technology of this type.

The technology described above is, however, subject to the problem that the measurement of X-ray fluorescence is affected by superimposed background radiation from singly or multiply inelastically scattered X-ray quanta. In this context, a method is known from U.S. Pat. No. 5,497,407, by means of which the components and quantities of an X-ray fluorescence material can be determined in a sample. In this method, the X-ray fluorescence component of the secondary radiation coming from an excited sample is determined by approximation by irradiating a plurality of reference samples without the material to be identified and calculating an average from the resulting secondary radiation. This average is then subtracted from the measured value of the sample to be examined as a background value due to other scattering processes. This method can, however, not be used when examining patients, because in this case there are no reference volumes without the XRF marker available.

In view of this background, it was an object of the present invention to provide means for the more accurate determination of X-ray fluorescence radiation, which can, in particular, be used when mapping the distribution of an XRF marker in a body volume.

This problem is solved by a device with the features of claim 1 and by a method with the features of claim 9. Advantageous designs are described in the dependent claims.

The device according to the invention for mapping the distribution of an XRF marker in a body volume, such as an organ of a patient, comprises the following components:

An X-ray source for the emission of a beam of rays directed onto the body volume, said beam comprising a first ray component with a quantum energy above the K-edge of the XRF marker and a second ray component with a quantum energy below the K-edge of the marker. In detail, this means that the spectrum of the quantum energies in the first ray component (essentially) only contains quantum energies lying above the K-edge, while the corresponding spectrum of the second ray component lies completely below the K-edge.

A detector for the detection of secondary radiation from the body volume, said detector being located outside the beam of rays of the X-ray source. In this context, the term "secondary radiation" includes any radiation generated by the interaction between the (primary) quanta from the beam of rays of the X-ray source and the body volume. Secondary radiation therefore in particular includes singly or multiply elastically or inelastically scattered radiation and the presently relevant X-ray fluorescence radiation caused by the absorption of primary quanta and the subsequent re-emission of an XRF quantum.

Means for adjusting the intensity ratio between the first and second beam components in the beam of rays of the X-ray source. In the extreme case, the intensity of a beam component can be significantly reduced if required.

With the device described above, the body volume to be examined can be irradiated with two spectrally different ray components, these being a first ray component causing the excitation of the X-ray fluorescence of the XRF marker, and a second beam component incapable of inducing such X-ray fluorescence. The second beam component will therefore exclusively cause secondary radiation without any X-ray fluorescence components. Since the intensity ratio between the first and second components can be adjusted, the relationship between secondary radiation without any fluorescence components (hereinafter referred to as "background radiation") and X-ray fluorescence radiation is adjustable as well. This in turn can be used to determine the X-ray fluorescence radiation component within the overall secondary radiation, which will be explained in greater detail below with reference to several preferred embodiments of the invention. The device offers the particular advantage that changes to the body volume are unnecessary and only the operating mode of the device is varied. The device is therefore particularly suitable for use within medical procedures involving molecular imaging.

The means for the adjustment of the intensity ratio between the first and second ray components can be implemented in various ways. The beam of rays in the X-ray source could, for instance, be generated by exciting various targets containing different quantitative proportions of sources of a first or second spectrum respectively. The sum of the radiation emitted by such a source would therefore depend on the quantitative proportions of the sources. In a particularly preferred design, the means for the adjustment of the intensity ratio include a filter removably located in the beam of rays in front of the body volume. The beam of rays entering the body volume then has a different spectral composition, depending on whether it has previously passed through the filter. The filter is preferably adjusted for strong absorption of any radiation above the K-edge of the XRF marker to be checked, while virtually completely passing any other radiation.

According to a preferred design, the filter referred to above is made of the material of the XRF marker to be checked or contains said material. In this case, the filter has to absorb radiation precisely from the K-edge of the XRF marker, with the result that the use of the filter correspondingly attenuates the first ray component and thus reduces the induction of X-ray fluorescence.

According to a preferred design of the X-ray source, the first ray component and/or the second ray component are/is monochromatic or quasi-monochromatic, the (average) quantum energy of said ray component deviating by less than 10%, preferably by less than 3%, from the energy of the K-edge of the XRF marker. It is in particular preferred if both the first and the second ray component are (quasi-) monochromatic, the spectral maximum of the first ray component lying slightly above and the spectral maximum of the second ray component lying slightly below the K-edge of the XRF marker. The close spectral proximity of the first and second ray components offers the advantage that all scattering processes with the exception of X-ray fluorescence run almost identically for both ray components, so that the ray components produce the same percentage of background radiation and the same spectral path. Regarding the excitation of X-ray fluorescence, there are, however, major differences between the ray components, because fluorescence can only be induced by the first ray component. By largely suppressing the first ray component, the proportion of background radiation can therefore be measured.

According to another preferred design, the X-ray source includes as target an element with a $K_{\alpha 1}$-line representing the first ray component and a $K_{\alpha 2}$-line representing the second ray component. The ray components generated by the simultaneous emission of the $K_{\alpha 1}$- and the $K_{\alpha 2}$-lines are therefore monochromatic or quasi-monochromatic. The element is preferably selected in such manner that its $K_{\alpha 1}$-line lies immediately above and its $K_{\alpha 2}$-line lies immediately below the K-edge of the marker to be checked.

The detector of the device is preferably designed for measuring the secondary radiation in a location- and/or energy-resolved manner. An energy-resolved (i.e. spectral) measurement offers the advantage that secondary radiation can be determined at specific XRF emission lines, while other components of the spectrum due to background radiation can be excluded. The energy resolution of the detector expediently does not have to fulfill the highest accuracy standards, because the component of X-ray fluorescence radiation in the secondary radiation can be determined with the device in another way. For this reason, the relatively expensive semiconductor detectors can be replaced by detectors with a scintillation crystal (e.g. NaI) or a gamma camera.

A location-resolved measurement offers the advantage that the geometrical point of origin of the measured secondary radiation can be determined more precisely, which is a precondition for imaging methods. The detector may, for instance, incorporate collimators defining parallel lines of sight running into the body volume. When radiation is detected in a specific cell of the collimator, its direction can therefore be determined.

According to a further aspect, the device incorporates a second detector located, in contrast to the first detector, in the beam of rays of the X-ray source and capable of the location-resolved measurement of the transmission radiation through the body volume. With the second detector, a conventional X-ray projection image can be produced for imaging morphological structures. This means that the device can, owing to primary irradiation, simultaneously produce an image of the molecular distribution of an XRF marker and a conventional morphological X-ray image.

The components of the device—these being the X-ray source and the secondary radiation detector as well, if required, as the second detector referred to above—are expediently permanently joined to one another by mechanical means and pivoted about an axis of rotation. The entire imaging mechanism of the device can therefore be rotated about a body volume to be surveyed while the relative geometrical location of its components remains constant. In this way, a (two- or three-dimensional) section through the body volume can be produced using the reconstruction algorithms of computer tomography known from prior art.

The invention further relates to a method for the determination of the distribution of an XRF marker in a body volume, said method comprising the following steps:

a) The irradiation of the body volume with a beam of rays with a first ray component with a quantum energy above the K-edge and a second ray component with a quantum energy below the K-edge of the XRF marker.

b) The measurement of the first secondary radiation from the body volume resulting from the irradiation by said beam of rays, preferably at a point outside the beam of rays.

c) The further irradiation of the body volume with the beam of rays, however with a different intensity ratio between the first and second ray components.

d) The measurement of the second secondary radiation from the body volume generated by the changed beam of rays (preferably at a point outside the beam of rays, in particular at the same point as in step b).

e) The determination of those components of the secondary radiation which are essentially exclusively due to the fluorescence of the XRF marker by comparing the first and second measured secondary radiations.

The method can in particular be implemented with a device of the type referred to above; with regard to the explanation of details, advantages and further aspects, the above description therefore applies. By irradiating the body volume in two different ways, each time with a different value for the first ray component exciting X-ray fluorescence, the background radiation component can be separated. X-ray fluorescence radiation can therefore be determined with a high degree of accuracy.

According to a preferred embodiment of the invention, the (first and second) secondary radiation is measured at a point where only multiple scattering is detected. Multiple scattering without single scattering components is mainly observed in the backscatter direction, in the scatter spectrum above the single-scatter Compton peak of primary radiation. The term "backscatter" covers radiation at an angle of more than 90° relative to the incoming primary radiation. In this case, at least one of the secondary radiation spectra is determined by a mathematical approximation function. Since multiple scattering is known to be the result of multiple scattering processes of the primary quanta, it is essentially independent of the geometry of the examined body volume. In view of this, an approximation of the secondary radiation spectrum by means of a function is likewise independent of the body volume. The use of a noise-free function ensures that the statistical noise in the signal is not increased further when calculating the fluorescence signal.

These and other aspects of the invention are apparent from and will be elucidated with reference to the embodiments described hereinafter.

Figure 1:
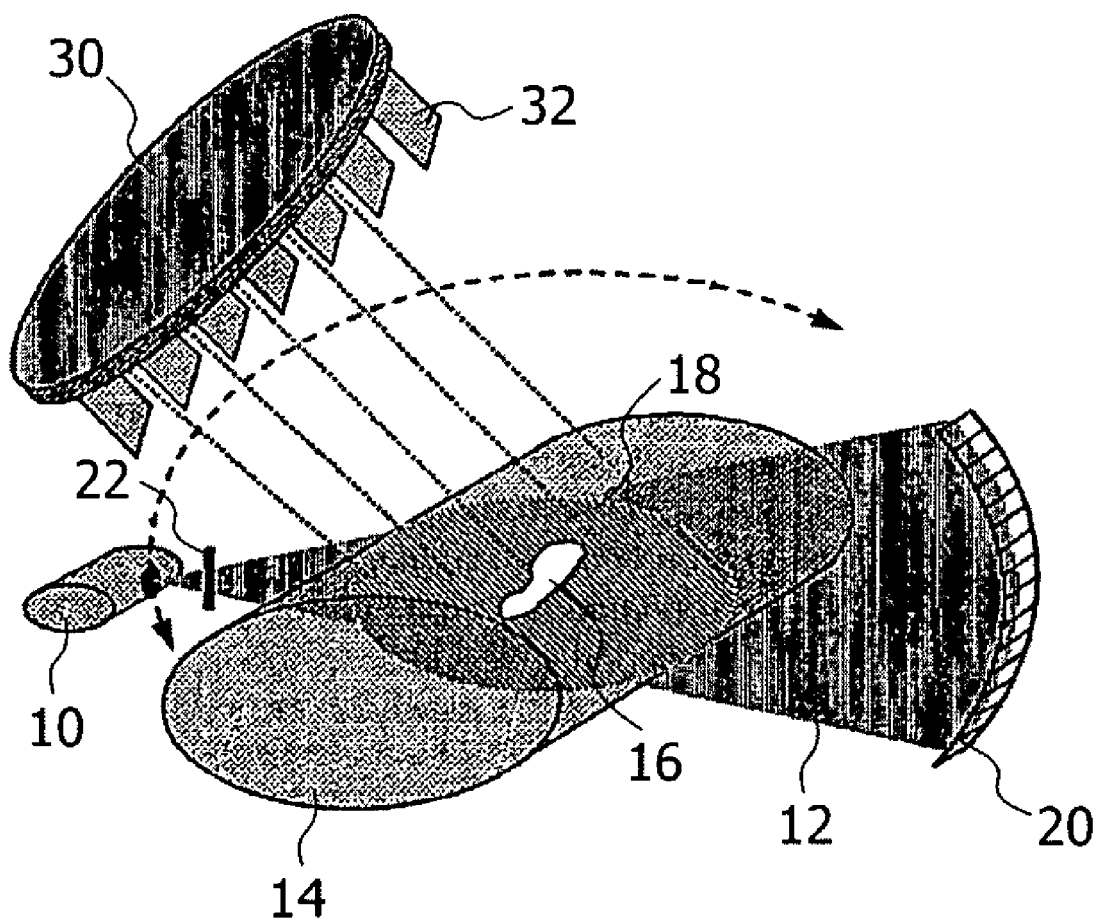
FIG. 1 is a diagrammatic representation of a device according to the invention with a transmission detector for showing an X-ray projection.

With the device shown in FIG. 1, it is simultaneously possible to produce a morphological image of a body volume 14 and a molecular image of the distribution of an XRF marker 16 in said volume 14. For this purpose, the device comprises an X-ray source 10, such as a Fluor'X appliance from Panalytical, wherein a target is hit by an electron beam. The target then emits X-ray radiation leaving the source 10 as a fan-shaped beam of rays 12. After penetrating the body 14, the beam 12 meets a line-shaped transmission detector 20 for the location-resolved measurement of the ray intensity arrived there. In this way, an X-ray projection can be produced, wherein each image point on the transmission detector 20 renders the integral of X-ray absorption in the body 14 along the connecting line from the image point to the X-ray source 10.

The body volume 14 further contains a distribution of an XRF marker 16 excited to emit X-ray fluorescence by the primary radiation of the beam of rays 12. To detect this X-ray fluorescence radiation, a further detector 30 is provided outside the beam of rays 12, this being designed as a gamma camera in the illustrated embodiment. In front of the sensitive surface of the camera 30, there is a collimator 32 with parallel blades. The height of the blades is typically 100 mm at a spacing of 5 mm. The collimator ensures that the (secondary) radiation impinging on the detector surface between two blades is limited to a defined narrow solid angle, allowing the location-resolved measurement of this radiation.

However, not only the X-ray fluorescence radiation to be detected arrives at the detector 30, but also some further background radiation caused by single or multiple scattering processes of the primary quanta. Background radiation and X-ray fluorescence together represent the secondary radiation from the body volume 14 which is detected by the detector 30. For the precise determination of the distribution of the XRF marker 16 in the body volume, a very precise knowledge of the X-ray fluorescence radiation from the body volume is required. This, is, however, made difficult when using the detector 30 by the co-detected background radiation.

To solve this problem, a method is presented below, by means of which the background radiation component of the secondary radiation can be determined. By way of example, it is assumed that the XRF marker 16 is based on the heavy metal gadolinium Gd, which is integrated into a pharmacologically active substance. The distribution of this substance in the body can then be used as an indicator, for instance for metabolic processes. Like any XRF marker, Gd requires a minimum energy of the impinging radiation if X-ray fluorescence is to be induced. This energy is defined by the so-called K-edge of the element and corresponds to the energy required to release an electron from the lowest energy level of the atom. The K-edge for Gd lies at 50.239 keV.

The X-ray source 10 is designed to emit a beam of rays 12 with two components. A first ray component has a quantum energy above said K-edge, while the second ray component has a quantum energy below the K-edge. The ray components are preferably monochromatic, with a wave length near the K-edge. In particular, the first ray component can be produced by the $K_{\alpha1}$-line of thulium Tm and the second ray component by its $K_{\alpha2}$-line. These lines are close to the K-edge of Gd (Tm $K_{\alpha1}$=50.73 keV, Tm $K_{\alpha2}$=49.76 keV). As the energy difference between the two lines is only approximately 2%, identical scattering processes produce a quasi-identical background radiation spectrum (with the proviso that "background radiation" as defined in the present context does not include any X-ray fluorescence components).

Figure 2:
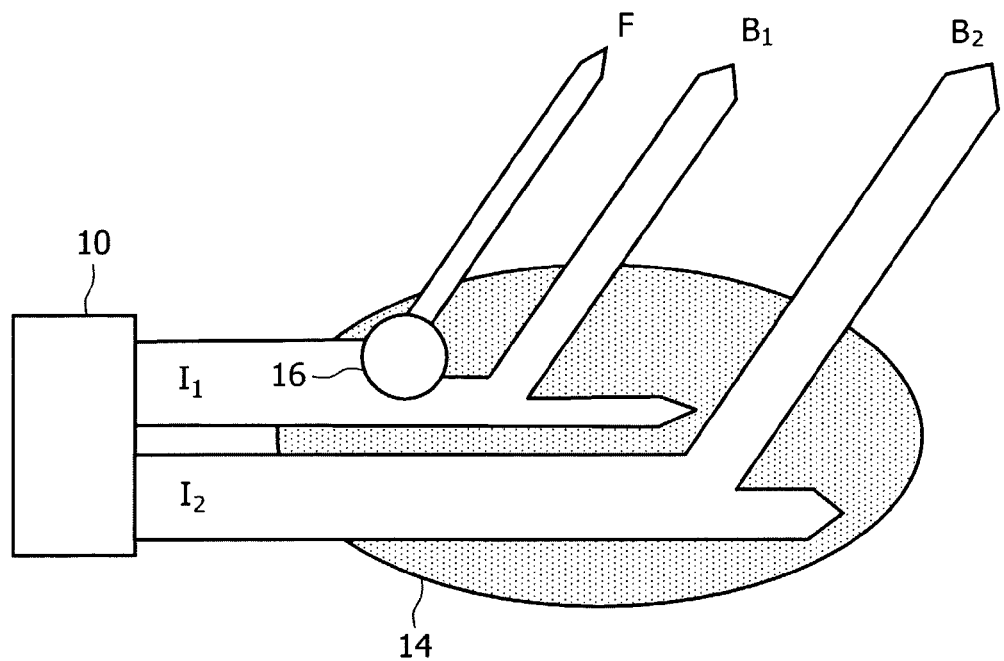
FIGS. 2 and 3 show intensity streams of primary and secondary radiation without (FIG. 2) and with (FIG. 3) a filter in the ray path.

FIG. 2 is a diagrammatic representation of the intensity streams of the two ray components from the source 10. The first component associated with the $K_{\alpha1}$-line has an intensity $I_1$, from which a background radiation component $B_1$ is abstracted in the body volume 14 by scattering processes and an X-ray fluorescence component F is abstracted by interaction with the XRF marker 16. The second component associated with the $K_{\alpha2}$-line has an intensity $I_2$, from which a background radiation component $B_2$ is abstracted in the body volume 14. The second ray component dues not generate any X-ray fluorescence radiation, because the energy of the primary quanta involved is too low.

With the variables shown in FIG. 2, the total secondary radiation $S_T$ measured by the detector 30 can be expressed as follows:

$$S_T = F + B_1 + B_2 \quad (1)$$

As the quantum energy values of the first and second ray components lie close to one another as explained above, in good approximation the same percentage of the associated intensities is converted into background radiation. As a result, the following equation applies by approximation:

$$B_1/B_2 = I_1/I_2 \quad (2)$$

In this context, it is assumed that the ratio $I_1/I_2$ of the two intensities $I_1$ and $I_2$ of the ray components leaving the source 10 is known or can be determined.

To calculate the required X-ray fluorescence component F, the proposed method comprises a second measurement with a different ratio of the intensities radiated into the body volume 14, thus changing the relative components of X-ray fluorescence and background radiation. Such a change in the intensity ratio can be achieved by introducing a suitable filter 22 into the ray path of the X-ray source 10, the filter 22 absorbing radiation above the K-edge much more strongly than radiation below this energy threshold. Such a filter characteristic is most easily implemented by making the filter 22 from the same material as the XRF marker, in the present case Gd.

Figure 3:
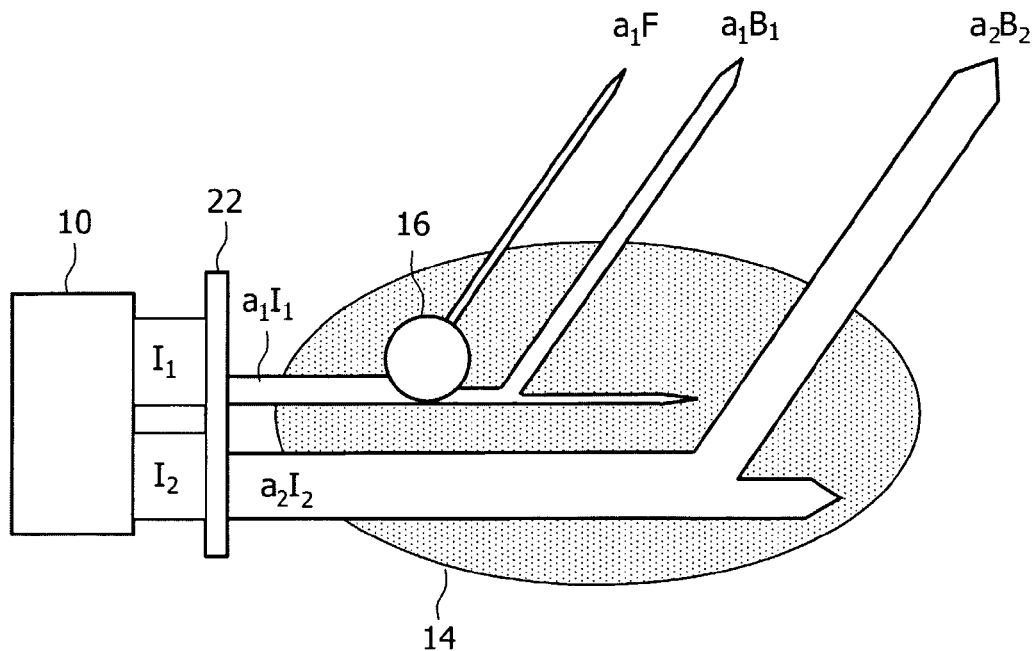

As FIG. 3 shows, the filter 22 allows only a greatly reduced component $a_1 I_1$ of the intensity $I_1$ of the first ray component ($K_{\alpha1}$-line) to penetrate the body volume 14. Of the intensity $I_2$ of the second ray component, a component $a_2 I_2$ leaves the filter 22, wherein $a_1$ has to be $\ll a_2$. The factors $a_1$, $a_2$ can be calculated in accordance with the following formulae:

$$a_1 = \exp(-\mu_1^{Gd} \cdot w) \quad (4)$$

$$a_2 = \exp(-\mu_2^{Gd} \cdot w) \quad (5)$$

wherein $\mu_1^{Gd}$ is the absorption coefficient of the Gd filter at the $K_{\alpha1}$-line of Tm, $\mu_2^{Gd}$ is the absorption coefficient of the Gd filter at the $K_{\alpha2}$-line of Tm and w is the thickness of the filter 22, all of which variables should be known.

FIG. 3 further indicated that the filtered ray components generate a secondary radiation $S_B$ detected in the detector 30 and having the following additive composition:

$$S_B = a_1 F + a_1 B_1 + a_2 B_2 \quad (6)$$

Three equations (1), (2) (6) are therefore available in total for calculating the unknown variables $B_1$, $B_2$ and F; in the present context, the most relevant of these is the X-ray fluorescence signal F.

While the invention has here been explained using Gd as an example for an XRF marker, other systems with similar characteristics are feasible. Erbium Er with a K-edge at 57.48 keV, for instance, is a suitable XRF marker, with dichromatic X-ray radiation being produced by the $K_{\alpha1}$-line (57.52 keV) and the $K_{\alpha2}$-line (56.27 keV) of tantalum Ta.

The application of the background radiation compensation described above increases statistical noise in the calculated fluorescence spectrum F. To reduce this effect, the detector 30, as shown in FIG. 1, preferably measures the backscatter, which is defined as having a scattering angle of >90° relative to the primary radiation. The fact that in backscatter the only contribution to the quantum energy range of the primary radiation is made by multiple scatter is known. For this reason, the shape of the background is independent of the exact geometry of the scatter object. The background spectrum $S_B$ can therefore be approximately determined mathematically by curve fitting using standard algorithms, for instance by means of a polynomial of the third order. The adapted curve is free of statistical noise (apart from the estimating accuracy of the polynomial coefficients), so that the subtraction of background radiation does not increase the statistical noise in F. It is further possible to reduce the measuring time for the background spectrum, so that the overall measuring time and thus the patient dose are primarily determined by measuring the X-ray fluorescence spectrum $S_T$.

With the described method, there is further no need to use a semiconductor detector (such as Ge) with high energy resolution for imaging secondary radiation. Instead, a detector with a lower energy resolution, such as a scintillation detector (NaI), can be used. This reduces the cost of the detector significantly or alternatively allows for the use of a much larger detector with a better signal-to-noise ratio. Conventional gamma cameras 30 (see FIG. 1) of the Anger type with a quantum energy resolution of $\leq 10\%$ and a location resolution in the millimeter range are particularly suitable for this application.

The entire device illustrated in FIG. 1, comprising the X-ray source 10, the filter 22, the transmission detector 20 and the detector 30 with the collimators 32, is further preferably pivotable about an axis of rotation through the body volume 14. The scan plane 18 can therefore be imaged on the two detectors 20, 30 at varying angles, permitting its two-dimensional reconstruction by means of known methods of computer tomography. It is, in particular, possible to provide first a morphological reconstruction of the body volume by means of the transmission detector 20 and then use the result of this reconstruction to determine the distribution of the X-ray marker 16.

The invention claimed is:

1. A device for mapping the distribution of an XRF marker (16) in a body volume (14), comprising an X-ray source (10) for the emission of a beam of rays (12), said beam comprising a first ray component ($I_1$) with a quantum energy above the K-edge of the XRF marker and a second ray component ($I_2$) (12) with a quantum energy below the K-edge of the marker, the quantum energy of the first ray component and the quantum energy of the second ray component deviating from the K-edge of the XRF marker by less than 10%; a detector (30) for the detection of secondary radiation from the body volume (14), said detector being located outside the beam of rays (12) of the X-ray source (10); means (22) for adjusting the intensity ratio between the first and second ray components in the beam of rays (12).

2. A device as claimed in claim 1, wherein the means for adjusting the intensity ratio include a filter (22) removably located in the beam of rays (12).

3. A device as claimed in claim 2, wherein the filter (22) contains the material of the XRF marker or is made there from.

4. A device as claimed in claim 1, wherein the first ray component ($I_1$) and/or the second ray component ($I_2$) are/is monochromatic or quasi-monochromatic.

5. A device as claimed in claim 1, wherein the first ray component is represented by the $K_{\alpha 1}$-line and the second ray component is represented by the $K_{\alpha 2}$-line of an element.

6. A device as claimed in claim 1, wherein the detector (30) is capable of the location-resolved and/or energy-resolved measurement of the secondary radiation.

7. A device as claimed in claim 1, wherein the device comprises a further detector (20) located in the beam of rays (12) and capable of the location-resolved measurement of transmission radiation through the body volume (14).

8. A device as claimed in claim 1, wherein the device components are coupled to one another and together capable of pivoting about an axis of rotation.

9. A method for determining the distribution of an XRF marker (16) in a body volume (14), comprising the following steps: a) Irradiation of the body volume (14) with a beam of rays (12) with a first ray component ($I_1$) with a quantum energy above the K-edge and a second ray component ($I_2$) with a quantum energy below the K-edge of the XRF marker; b) Measurement of the resulting first secondary radiation from the body volume (14); c) Irradiation of the body volume (14) with the beam of rays with a different intensity ratio between the first and second ray components; d) Measurement of the resulting second secondary radiation from the body volume (14); e) Determination of the components of the secondary radiation which are due to the fluorescence of the XRF marker by comparing the first and second secondary radiations.

10. A method as claimed in claim 9, wherein the secondary radiation is measured at a point where only backscatter is detected, and in that at least one of the spectra of the secondary radiations is determined by approximation by means of a function.

* * * * *